United States Patent [19]
Marmer

[11] Patent Number: 6,056,671
[45] Date of Patent: May 2, 2000

[54] FUNCTIONAL CAPACITY ASSESSMENT SYSTEM AND METHOD

[76] Inventor: Keith S. Marmer, 24 Oakwood Dr., Medford, N.J. 08055

[21] Appl. No.: 08/989,919

[22] Filed: Dec. 19, 1997

[51] Int. Cl.[7] .................................................. A63B 21/00
[52] U.S. Cl. .................................. 482/8; 482/10; 600/595
[58] Field of Search ..................................... 600/595, 594; 128/898; 482/10, 8; 73/379.01, 379.02, 379.03, 379.04, 379.05, 379.06, 379.07, 379.08, 379.09; 601/23

[56] References Cited

U.S. PATENT DOCUMENTS

| | | |
|---|---|---|
| 4,416,293 | 11/1983 | Anderson et al. . |
| 4,667,513 | 5/1987 | Konno . |
| 4,813,436 | 3/1989 | Au . |
| 4,882,677 | 11/1989 | Curran .................................. 73/379.02 |
| 4,971,069 | 11/1990 | Gracovetsky ............................ 600/594 |
| 5,203,346 | 4/1993 | Fuhr ..................................... 600/595 X |
| 5,209,240 | 5/1993 | Jain et al. . |
| 5,441,047 | 8/1995 | David et al. . |
| 5,462,065 | 10/1995 | Cusimano . |
| 5,482,048 | 1/1996 | Johnson . |
| 5,524,645 | 6/1996 | Wills . |

OTHER PUBLICATIONS

Isernhagen Work Systems—Manual—pp. 15–17.
RMA—Industrial Rehabilitation Products & Services—Catalogue—winter 1993—p. 26.
Spinex Medical Technologies, Inc.—Expert Vision Spinoscope, Technology for the Control of back–related claims—Brochure.
The Polinsky Advantage, Functional Capacities Assessment—Brochure.
National Work Recovery Centers—Ergos Evaluation Summary Report—Sample Report—pp. 1–6.
Blankenship—The Blankenship FCE System—Report—1996—pp. 1–5.
Peak Performance Technologies Inc.—Motus Brochure—pp. 1–2—Englewood, CO.
Isotechnologies, Inc.—The Standard For Monitoring Back Motion—pp. 1–2.
Promatek Medical Systems—New Product Announcement—1 page.
ErgoScience The Physical Work Performance Evaluation—p. 11.
Med–Data Systems, Inc.—The Computest Program—Brochure—1 page.
Sunmed—We can't give you just one reason . . .—Brochure—1 page.
J Tech Medical Industries—Put Your Practice on the Fast Track . . .—Brochure—2 pages—Heber City, Utah.
Key Functional Assessments, Inc.—Key Method Now you can expand your practice—Brochure—3 pages—Minneapolis, Minnesota.

(List continued on next page.)

*Primary Examiner*—Glenn E. Richmon
*Attorney, Agent, or Firm*—Walter J. Tencza, Jr.

[57] ABSTRACT

A system and method of objectively testing the functional capacity of a patient over a range of motion and with a limited resistance are provided. A selected number of visual indicators are applied and maintained at selected points with respect to the patient. The patient is directed through a series of exercise movements. The patient's movements are captured on a video record. This video record is digitized. The motion of the indicators is tracked in the digitized video record. A patient data set is developed including performance parameters based, at least in part, on the position and the time of each indicator during the movements. The patient data set is compared to a base data set. If the patient's performance parameters fall within certain ranges, it can be determined that the patient is or is not exerting a true effort. The functional capacity of the patient is determined based, at least in part, on the comparison of the patient data set with the base data set.

25 Claims, 3 Drawing Sheets

OTHER PUBLICATIONS

Mital, Anil—Comprehensive maximum acceptable weight of lift database for regular 8–hour work shifts—Paper—Feb. 13, 1984—12 pages—Dept. of Mechanical and Industrial Engineering. University of Cincinnati, Cincinnati, Ohio.

Ayoub, M.M.—Review, Evaluation, and Comparison of Models for Predicting Lifting Capacity—Human Factors—1980, 257–269; 22(3); Department of Industrial Engineering. Texas Tech University, Lubbock, Texas.

Mital, Anil—Maximum weights of lift acceptable to male and female industrial workers for extended work shifts—*Erogonomics*, 1984, vol. 27; No. 11, 1115–1126—Department of Mechanical and Industrial Engineering, University of Cincinnati, Cincinnati, Ohio.

Ciriello, V.M., et al.,—The effects of task duration on psychophysically–determined maximum acceptable weights and forces—Article—12 pages—Taylor & Francis, Ltd.

Asfour, Shihab, et al.,—Physiological Guidelines for the Design of Manual Lifting and Lowering Tasks: The State of the Art—American Industrial Hygiene Association; 1988; vol. 49(4); pp. 150–160.

Snook, S.H. and Irvine, C.H.—Maximum Acceptable Weight of Lift—American Industrial Hygiene Association Journal; 1967; pp. 322–329.

Mital, Anil and Fard, Hamid—Psychophysical and physiological responses to lifting symmetrical and asymmetrical loads symmetrically and asymmetrically—Journal Article—1986—11 pages.

Garg, Arun and Saxena, U.—Effects of lifting frequency and technique on physical fatigue with special reference to psychophysical methodology and metabolic rate—1979—10 pages.

Marras, PhD, W.S. and Wengram, M.D., P.E.—Flexibility and Velocity of the Normal and Impaired Lumber Spine—Archives of Physical Medicine and Re–Habilitation—pp. 213–217.

Marras, W.S. et. al.—Accuracy of a three–dimensional lumbar motion monitor for recording dynamic trunk motion characteristics—International Journal of Industrial Ergonomics; 1992, 75–87.

Park, Kyung S., and Chaffin, Don Bo.—Prediction of Load–lifting limits for manual materials handling—5 pages.

Mital, Anil—The Psychophysical Approach in Manual Lifting—A Verification Study—Human Factors—Oct. 1983; pp. 486–491.

FIG. 6

| asending rep 41 | aspect of rep | p value | consistent | sub-consistent | inconsistent |
|---|---|---|---|---|---|
| 1 | PEAK V | .000 | <-4.5 | -4.5 to -2.8 | >-3.8 |
| 2 | MEAN V | .000 | <-2.8 | -2.8 to -2.3 | >-2.3 |
| 2 | PEAK V | .000 | <-4.4 | -4.4 to -3.7 | >-3.9 |
| 3 | MEAN V | .000 | <-2.9 | -2.9 to -2.2 | >-2.2 |
| 3 | PEAK V | .000 | <-4.5 | -4.5 to -3.4 | >-3.4 |
| 3 | TERM ACC | .000 | >2.0 | 1.0 to 2.0 | <1.0 |

| deasending | | | | | |
|---|---|---|---|---|---|
| 1 | PEAK V | .000 | >4.7 | 3.0 to 4.7 | <3.0 |
| 2 | MEAN V | .000 | >2.8 | 2.3 to 2.8 | <2.3 |
| 2 | PEAK V | .000 | >4.5 | 3.9 to 4.5 | <4.5 |
| 3 | MEAN V | .000 | >3.0 | 2.4 to 3.0 | <2.4 |
| 3 | PEAK V | .000 | >4.5 | 3.0 to 4.5 | <3.0 |
| 3 | TERM ACC | .000 | <-2.3 | -2.3 to -1.7 | >-1.7 |

FIG. 7

| asending rep 41 | aspect of rep | p value | consistent | sub-consistent | inconsistent |
|---|---|---|---|---|---|
| 1 | MEAN V | .000 | <-3.1 | -3.1 to -2.9 | >-2.9 |
| 1 | TERM ACC | .000 | >3.1 | 1.6 to 3.1 | <1.6 |
| 2 | MEAN V | .000 | <-3.7 | -3.7 to -2.5 | >-2.5 |
| 2 | PEAK V | .000 | <-5.4 | -5.4 to -5.1 | >-5.1 |
| 2 | TERM ACC | .000 | >2.8 | 1.7 to 2.8 | <1.7 |
| 3 | MEAN V | .000 | <-4.1 | -4.1 to -2.4 | >-2.4 |
| 3 | TERM ACC | .000 | >2.3 | 2.0 to 2.8 | <2.0 |

FIG. 8

| asending rep 41 | aspect of rep | p value | consistent | sub-consistent | inconsistent |
|---|---|---|---|---|---|
| 1 | PEAK V | .000 | <-2.1 | -2.1 to -1.4 | >-1.4 |
| 1 | TIME | .002 | <.60 | .6 to .8 | >.8 |
| 2 | TIME | .002 | <.7 | .7 to .82 | >.82 |

FUNCTIONAL CAPACITY ASSESSMENT SYSTEM AND METHOD

A portion of the disclosure of this patent document is subject to copyright protection. The copyright owner has no objection to the facsimile reproduction by anyone of the patent disclosure, as it appears in the Patent and Trademark Office patent files or records, but otherwise reserves all copyright and other rights whatsoever.

FIELD OF THE INVENTION

The invention is related to the field of human physical testing. In particular, the invention is directed to a method for assessing the functional capacity of an individual (such as a patient or a test subject), determining whether the individual is exerting a true effort and determining the maximal lifting capacity of the individual.

BACKGROUND OF THE INVENTION

In the field of physical medicine and rehabilitation, doctors and physical therapists are often called upon to assess the functional capacity of a particular patient. This may arise in the context of testing a company's new employees to determine whether they are physically capable of performing the tasks involved in a given job, testing previously injured employees to determine whether they are capable of returning to work, or testing those injured in an accident to determine the scope of the injury, such as for an insurance settlement or a law suit. Therapists typically run a series of tests, which can include physical tests, visual observations and verbal questions, to assess the ability of a patient to lift and move objects and/or to tolerate various postures, positions or activities. For clarity's sake, the test giver will be referred to as the "therapist" throughout. It will be appreciated that the test giver could be a doctor, nurse, physical therapist, exercise physiologist or other such person.

While there is a great need for an accurate functional capacity assessment, there currently exists no system which can repeatedly and accurately test the weight that a person can safely lift. This problem is compounded by an uncertain degree of effort on the part of the patient. In certain circumstances, the patient may believe it is in his best interests to exert a less than maximal effort. Consequently, the patient may refuse to lift a weight above a certain weight, may lift a weight slowly, may complain of pain during certain weighted movements (while not, in fact, in pain), or may otherwise adjust his performance in an attempt to reflect an injury. While current testing methods can provide some useful information when administered by a skilled therapist, if the dishonest patient is relatively consistent, it can be difficult to ascertain when he is faking and when the patient is exerting a true effort when the therapist relies exclusively upon current testing methods.

Current assessment protocols generally require the patient to proceed through a series of movements. Some of these movements employ only the body weight of the patient, or can be performed using isokinetic or isometric machines. Alternatively, the movements can be weighted, providing additional resistance to the patient. The therapist observes the movements of the patient, both how the torso and limbs move, as well as any facial expressions or other outward signals the patient may give. Using this information, the therapist determines what he or she believes to be the patient's maximal effort, whether that patient is faking their effort, and whether that patient is capable of returning to work. In other tests, the patient himself states when he believes he has lifted a maximum weight or performed a task to his fullest capacity. Obviously, these tests are highly subjective, relying on the skill of the therapist as well as the current physical and emotional states of the therapist and the patient. There are a variety of testing techniques that employ the above methodology. None of these tests have been fully standardized so as to eliminate subjectivity and bias. Each therapist administers the tests differently, affecting the patients and their responses to the tests, adding additional uncertainty. Because the results of the tests contain a high level of uncertainty, they can only be of limited value.

U.S. Pat. No. 4,813,436 is directed to a motion analysis system employing various operating modes and including a video camera. Markers are secured to the various joints of the test subjects body. Pressure sensitive shoes or insoles are worn by the subject as he walks or runs on a treadmill. The subject is video taped using two distinct video cameras. The video signal is stored and then processed to provide digitized data concerning the movement of the markers. Meanwhile, the pressure sensitive insoles provide signals which indicate the pressure applied by the subjects foot while on the treadmill. The digitized information from the video cameras is used to display the gait, the angular position of the various joints of the patient and other information related to the walking characteristics of the subject.

U.S. Pat. No. 4,416,293 is directed to a method and apparatus for recording gait analysis in podiatric diagnosis and treatment. The subject is instructed to walk or run on a treadmill while being video taped. This video is displayed for review by the subject and the physical therapist.

U.S. Pat. No. 5,524,645 is directed to an objective measurement tool for evaluating medical therapy outcome in accordance with quantified physical therapy data. Once the physical parameters have been established, they are tracked during physical therapy. A measure of the patient's progress can, therefore, be calculated. This measure can be used to justify additional physical therapy or to indicate when further physical therapy would not be particularly effective.

None of these systems solve the problems addressed by the system and method of the current invention. Further, various prior art systems are large and expensive and therefore not well-suited to on site testing.

SUMMARY OF INVENTION

It is an object of an aspect of the instant invention to provide a method of safely assessing the functional capacity of a patient with a high level of certainty.

It is another object of an aspect of the instant invention to provide a functional capacity assessment method which can provide quantifiable and repeatedly consistent results while indicating whether the patient is exerting a true or "consistent" effort.

It is another object of an aspect of the invention to provide a system that can determine the maximal lifting ability of a subject without requiring a maximal lifting effort.

It is another object of the invention to provide a system of assessing functional capacity which can be easily transported and operated in the field.

It is another object of the invention to provide a method of assessing functional capacity which reduces the effect of having different therapists administer the tests.

It is another object of an aspect of the invention to provide a system which can quickly and consistently evaluate the effort of a patient while predicting the patient's functional capacity when working over an extended period of time.

It is another object of the invention to provide an objective test to assess the functional capacity of the patient while allowing the consideration of subjective factors when appropriate.

It is another object of the invention to develop objective, consistent test results which can be stored for later use and analysis. Such a system permits reproduction of test results and proof of the validity of the tests.

In accord with one aspect of the invention, a method of objectively testing the functional capacity of a patient over a range of motion and with a limited resistance is provided. A selected number of visual indicators are applied and maintained at selected points with respect to the patient. The patient is directed through a series of exercise movements. The patient's movements are captured on a video record. This video record is then digitized. The motion of the indicators is tracked in the digitized video record. A numerical patient data set is developed including performance parameters based, at least in part, on the position and the time of each indicator during the movements. The patient data set is compared to a numerical base data set. The consistency of effort of the patient is determined based on the comparison of the patient data set with the base data set.

Certain implementations of this aspect of the invention provide that: a selected resistance to the series of movements is provided; the resistance during the series of movements is altered; the resistance is increased at a predetermined, controlled rate during the series of movements; developing the patient data set comprises calculating a first derivative with respect to time of the position of the indicators in a vertical direction; an average first derivative over a portion of the series of the exercise movements is determined, which average first derivative is a patient performance parameter that is compared to a base average first derivative in the base data set; a peak first derivative over a portion of the series of the exercise movements is determined, which peak first derivative is a patient performance parameter that is compared to a base peak first derivative in the base data set; developing the patient data set comprises calculating a second derivative with respect to time of the position of the indicators in a vertical direction; a terminal second derivative over a portion of the series of the exercise movements is determined, which terminal second derivative is a patient performance parameter that is compared to a base terminal second derivative in the base data set; the indicator is attached to a box and the series of movements comprise grasping a handle attached to the box, bending at the waist, moving the handle from near a ground level to a waist level, and returning the handle to near ground level; the indicator is attached to a box and the series of movements comprise grasping a handle attached to the box, moving the handle from waist level to an overhead position, and returning the handle to waist level; the indicator is attached at the waist of the patient's body and the movements comprise starting at a standing position, squatting, and then standing again.

In accord with another aspect of the invention, a method for assessing the functional capacity of a patient by moving a lifting platform over a predetermined series of exercise movements is provided. The patient is directed to grasp the lifting platform. The patient is also directed to move the lifting platform from a first level to a second level. Selected resistance is added to the lifting platform. This movement is repeated for a number of repetitions. The motion of the lifting platform is recorded on a motion record. A patient data set is created including selected performance parameters corresponding, at least in part, to the position of the lifting platform at a time during movement. The patient data set is compared with a standard data set. The functional capacity of the patient is determined based, at least in part, on the comparison of the patient data set with the standard data set.

Certain implementation of this aspect of the invention provide that: the motion record is digitized and the movement of a particular point on the lifting platform is tracked, and the patient data set includes performance parameters based, at least in part, on the movement of the particular point; an indicator is applied on the particular point; the first level is at the patient's waist height and the second level is over the patient's head; the first level is near a ground level and the second level is at the patient's waist; the directions to the patient are provided by a computer processor through a speaker; the directions to the patient are provided by a computer processor through a video display; the patient is directed to move the lifting platform from the second level to the first level; the motion of the lifting platform is recorded as pictures by a video tape camera, the method further comprising digitizing the pictures into digitized information, and storing the digitized information in a computer memory; the patient data set includes determining the speed of the lifting platform in a vertical direction; the standard data set is created including directing a limited group of people to exert a true effort, performing and recording the exercise protocol, and determining ranges of performance parameters indicative of a true effort to a selected level of statistical confidence; comparing the patient data set with the standard data set includes comparing the performance parameters of the patient with the true effort range; the limited group of people share a common attribute; the common attribute is that the people in the limited group are healthy, have the same job or have suffered the same injury; creating the standard data set further comprises directing a limited group of people to exert a false effort, performing the exercise protocol, and determining ranges of performance parameters indicative of a false effort to a selected level of statistical confidence; comparing the patient data set with the standard data set includes comparing the performance parameters of the patient with the false effort range; determining the functional capacity of the patient is based, at least in part, on whether the patient performance parameters fall within the true effort range or the false effort range.

In accord with another aspect of the invention, a system is provided for assessing the physical capacity of a patient. Means are operably engaged to a set of handles for resisting movement of the handles. An indicator is disposed at a fixed position with respect to the handles. Recorder means are disposed proximate the indicator for recording the locations of the indicator as a function of time. The locations of the indicator over time as recorded by the recorder means are digitized. Means are also provided for creating a patient data set based, at least in part, on the digitized locations of the indicator. Means for storing a standard data set corresponding to the locations of the indicator over time for a functionally capable person are also included. Means are provided for comparing the patient data set to the stored standard data set to obtain a result. This result is communicated to the therapist.

BRIEF DESCRIPTION OF THE DRAWINGS

FIG. 6 is a table showing the ranges of parameters for patient moving the lifting platform from near ground level to waist height.

FIG. 7 is a table showing the range of parameters for a patient moving the lifting platform from waist height to overhead.

FIG. 8 is a table showing the range of parameters for a patient squatting.

DESCRIPTION OF PREFERRED EMBODIMENTS

Figure 1:
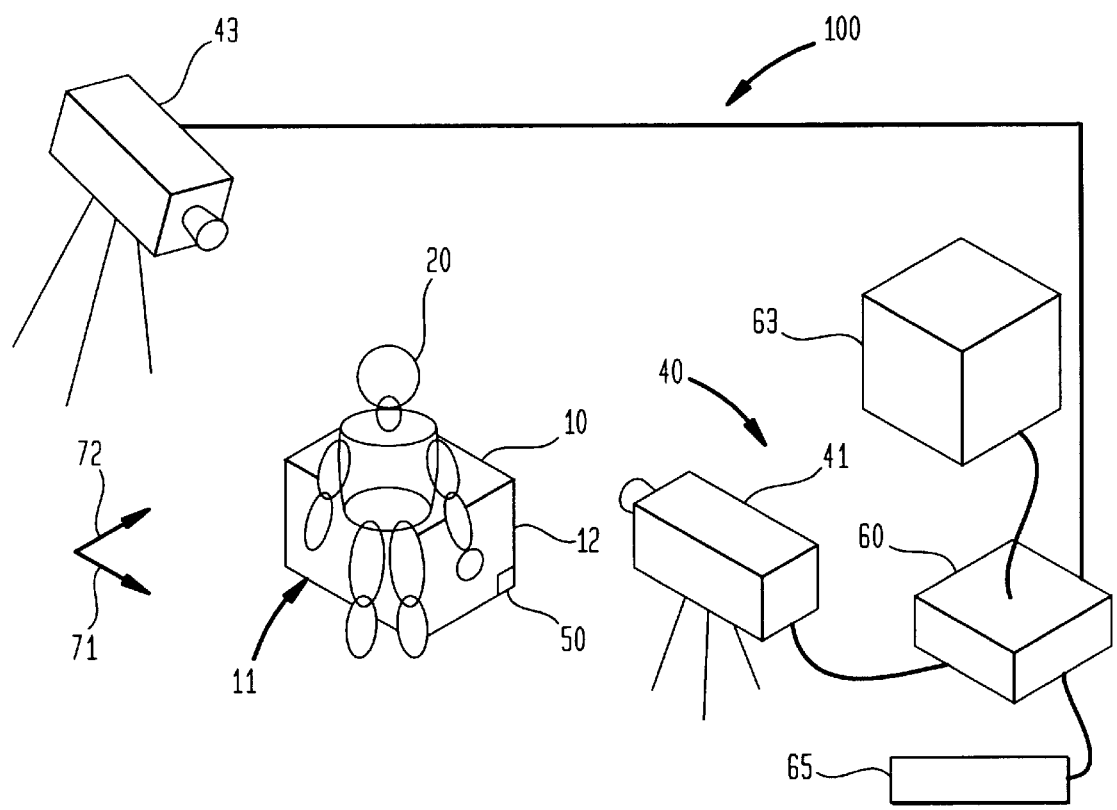
FIG. 1 is a perspective view of the system for performing the method of the current invention.

FIG. 1 depicts a functional capacity assessment system 100 for use with the method of the instant invention. As will be discussed more fully below, this system permits the therapist to test the patient with various exercise protocols and make a record of the performance. The system also creates a quantifiable, numerical description of the patient's performance, referred to as "parameters". This description can be put in a patient data set for comparison to a base data set. In one application, the performance parameters are compared to determine if the patient is exerting a true effort. In other applications, the performance parameters are compared to determine the maximal lifting strength or endurance of the patient. This information can be used as part of the functional capacity assessment.

A lifting platform 10 is positioned in front of the patient 20 at a selected height. The therapist 30 or assistant (see FIG. 2) is positioned adjacent the lifting platform such that she can add additional weights 31 to the lifting platform, as discussed below. As currently preferred, the lifting platform comprises a box 11 with handles 12 located on its sides for the patient to grasp. This box weighs about one pound when empty. Such a box is particularly adapted to receive additional weights during an exercise protocol.

It will be appreciated that other lifting platforms 10 can also be employed and still practice the invention. A handle bar or other device which can be easily gripped by the patient 20 may be operably engaged to various resistance means, such as those commonly used for exercise purposes. For example, a bar attached to a weight stack, rubber resistance bands, potentiometer or an ergometer can be employed. It is important that the handle and resistance means provide the patient with the freedom to move the handle in space against a controlled resistance at a speed determined by the patient (and, of course, by the patient's ability). Preferably, the handle is movable through three dimensions of space but, in certain applications, it may be desirable to limit the movement of the handle to one or two dimensions. In that case, the handle can be attached to a track or other means for controlling its movement, as one skilled in the art would appreciate. For example, when used in geriatric testing, it may be important to limit the degrees of freedom of handle movement and such a specific application could be developed and still practice the invention.

A device 40 for capturing and recording the movement of the lifting platform 10 or the patient 20 is positioned proximate to the lifting platform. As currently preferred, a video camera 41 is positioned perpendicular to the forward-facing direction of the patient. This camera is disposed about five feet from the lifting platform. Indicators 50 or markers are positioned at selected points on the lifting platform and the patient. The positioning of the camera is not critical so long as the indicators are clearly visible. The video camera captures the movement of patient and/or lifting platform and, in particular, the indicators, for analysis. It is easier for the functional capacity assessment system 100 to track the movement of the visually distinct indicators, rather than selecting a point on the actual lifting platform or patient which may not be clearly distinguishable from adjacent portions of the video picture. It will be appreciated that different specific points on the lifting platform or patient can be tracked and still practice the invention. Further, multiple indicators can be attached to the lifting platform such that the platform's orientation over the exercise protocol can be observed and recorded.

Typically, the video camera 41 captures thirty frames per second, providing fairly detailed information about this movement. It should be appreciated that a camera with greater or less precision can be employed and still practice the invention. For example, for testing of certain fast but subtle movements, a faster, highly precise camera may be desirable. When analysis and storage of information by a computer processor (discussed below) is at a premium, it may be desirable to record less frames per second. Further, while visible light is currently being recorded by the video camera, in certain applications, it may be useful to use a camera which captures X-rays, thereby permitting the tracking of the movement of the patient's skeleton. Alternatively, a camera which capture infrared or other types of information can be employed, as is appropriate for that particular application.

Figure 2:
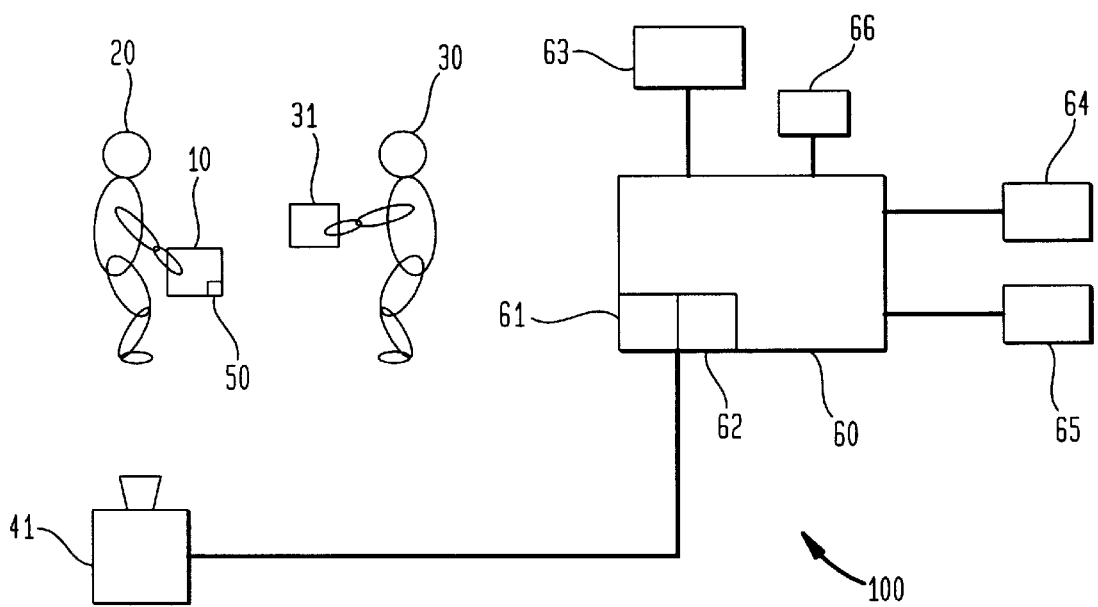
FIG. 2 is a schematic side view showing an embodiment of the system of FIG. 1.

Referring to FIG. 2, the video camera 41 is operably engaged via a video line to a computer processor 60. The computer processor includes a memory 61, such as a hard drive or DAT, and a data processing means 62, such as a microprocessor chip, and a timer. The computer processing means is controlled by software. Of course, other software could be employed and still practice the invention. A computer display 63, a printer 64 and a computer input device 65 are operably engaged to the computer processor. The input device may include a keyboard, a mouse, a signature pad, joy stick, touch pad, microphone or other such device. Currently, the computer is preferably any commonly available lap top computer, which adds to the portability of the system 100. of course, other computer systems can also be employed. Software for running the microprocessor is loaded in the memory or, alternatively, can be provided from an outside source such as a disk drive or the like, as is well known.

The video signal (that is, the picture or frame) captured and recorded by the video camera 41 is an analog signal. The signal is transmitted to the computer processor 60 where it is digitized. The digitization is performed by commercially available hardware and software on the data processing means, such as programs from FAST of Germany or Nogetech, as one skilled in the art would appreciate. Alternatively, a separate piece of hardware can be supplied to perform the digitizing or a video camera can be developed which records information digitally. This digitized information is preferably stored for analysis on the hard drive 61 or other computer memory device, such as a DAT, CD-ROM, or the like. The digitized information includes the position of the indicators 50 on the frame and the particular frame of the recorded video on which the indicator is located at that position. Since the frames are recorded at set time intervals (e.g., 30 times per second), the number of the frame can be used as a measure of time. Thus a data set is developed including both the position and time for the indicator during the exercise protocol.

Once the digitized information concerning the position and the time of the indicator 50 is collected, the computer processor 60 is used to calculate various parameters regarding the movement of the indicator 50. For example, the absolute velocity and absolute acceleration of the indicator in a vertical direction during a portion of the exercise protocol can be calculated. Further, the time at which the patient reaches a given position in the exercise protocol can also be determined. It will be appreciated that other such parameters describing the motion of the indicator can be determined or calculated, as a particular therapist desires, depending on the given application.

Audio speakers 66 and a video display 63 are operably engaged to the computer processor 60. Once the system 100 is actuated by the therapist 30, the central processing unit 62 will send signals to the audio speakers which will, in turn, broadcast previously recorded instructions to the patient 20 regarding performing the exercise protocol. These instructions can be recorded in several languages. Signals may be sent to the display 63 to provide additional, visual instructions to the patient if that is believed desirable. In any case, the instructions to perform the exercise protocol are delivered by the system via the audio speakers and the video display. This insures that the instructions are delivered in the exact same way to each patient, increasing the consistency of the testing results and minimizing any bias from the therapist.

A printer 64 may be operably engaged to the computer processing unit 60. The printer can be used to print out the results of the test or to provide further written instructions to the patient, if desired. A signature pad 65 can be provided to record the signatures of the therapist, patient, witnesses, etc., as desired, on the computer memory.

As currently preferred, a single video camera 41 is used to record the movement of the indicator. Consequently, the information concerning the indicator is limited to two dimensions, a horizontal direction 70 and a vertical direction 71. Additional cameras can be employed at offset locations to provide enough additional data to develop three dimensional information, including movement of the indicator 50 through a transverse direction 72. This may be particularly useful when the exercise protocol requires more complex movements by the patient, such as in a customized work-simulation exercise. Consequently, the patient data set may include information about the position of the indicator (or of a portion of the patient's body) in three dimensions over time. This information can be used to calculate various parameters, including information based, in part, on the position of the indicator in the transverse direction.

It is currently preferred that a second video camera 43 be provided. This camera is positioned to the side such that it will capture the entire functional capacity assessment, including the performance of the patient and the therapist. Preferably, the second video camera is freestanding and records images only on video tape. Of course, this second video camera can be operably engaged to the computer processor 60, such that its images are recorded on the hard drive 61. This second video camera insures that the assessment was run properly.

The therapist 30 can design an infinite number of exercise protocols to obtain information about the functional capacity of the patient 20. As currently preferred, the patient is put through a series of exercise routines or protocols, including three which are subjected to the video analysis of the instant invention. The patient determines the range of motion and level of effort employed, thus reducing the chance of injury. Further, the patient need not complete the entire series for the therapist to obtain valuable information. The motion of the indicator during these routines is recorded and analyzed by the system 100 of the invention.

Figure 3:
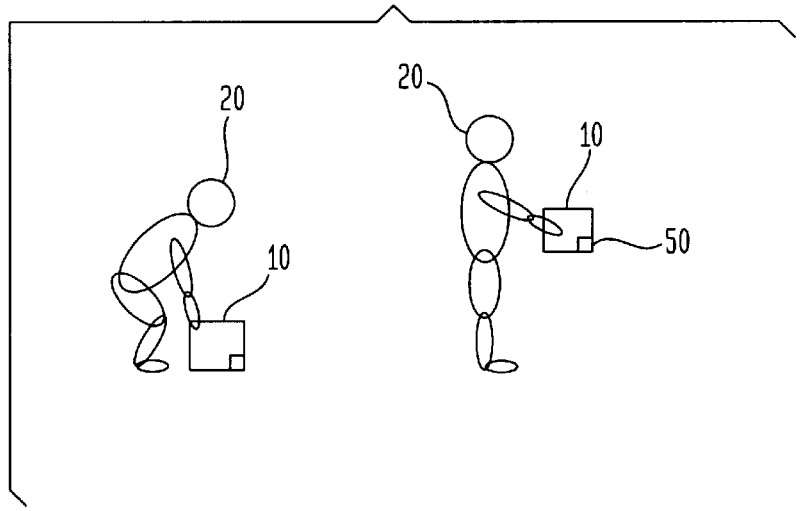
FIG. 3 is a schematic side view of an exercise protocol (i.e., lifting the platform from near ground level to waist height) for use with the system of FIG. 1.

Referring to FIGS. 1, 3 and 6 in the first series of exercises, the indicator 50, is attached to the side of the lifting platform 10 such that it is visible to the video camera 41. The lifting platform is positioned on the ground directly in front of the patient 20. The computer processor 60 is actuated (that is, the software which runs the system 100 is turned on). The computer processor in turn actuates the video camera 41 which begins recording pictures, including the position of the indicator. The computer processor also controls the speakers 66 and the video display 63, providing instruction to the patient regarding how the exercise protocol should be performed. In particular, the patient is instructed to grasp the lifting platform. The patient is then instructed to pick the lifting platform up to waist height at a comfortable pace and then return it to the ground. The box or lifting platform carries no additional weight during the first repetition. At the bottom of the motion, the therapist adds an additional weight 31 to the lifting platform. This lifting motion is repeated multiple times or until the patient cannot lift the weight or is uncomfortable lifting the weight. A very light weight, such as a three pound weight 51, is added to each repetition thereafter. Typically, the weight added after each repetition is the same, but this is not necessary.

Figure 4:
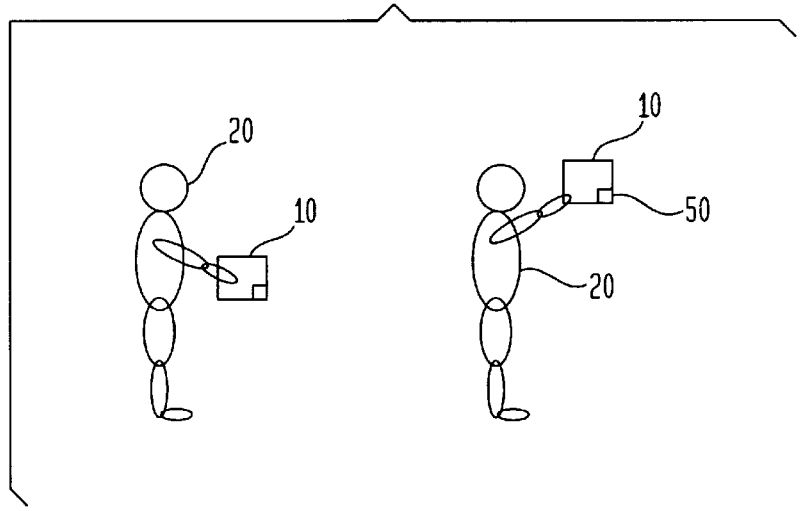
FIG. 4 is a schematic side view of another exercise protocol (i.e., lifting the platform from waist height to overhead) for use with the system of FIG. 1.

Referring to FIGS. 1, 4 and 7, n a second exercise protocol, the patient 20 holds the lifting platform 10 at waist height, lifts it to an overhead position and then returns it to waist height. This is repeated multiple times with the therapist adding a limited weight, such as three pounds, at the bottom of the movement. The indicator 50 is again placed on the side of the lifting platform adjacent to the video camera 41 and the instructions are delivered to the patient by the computer processor 60.

Figure 5:
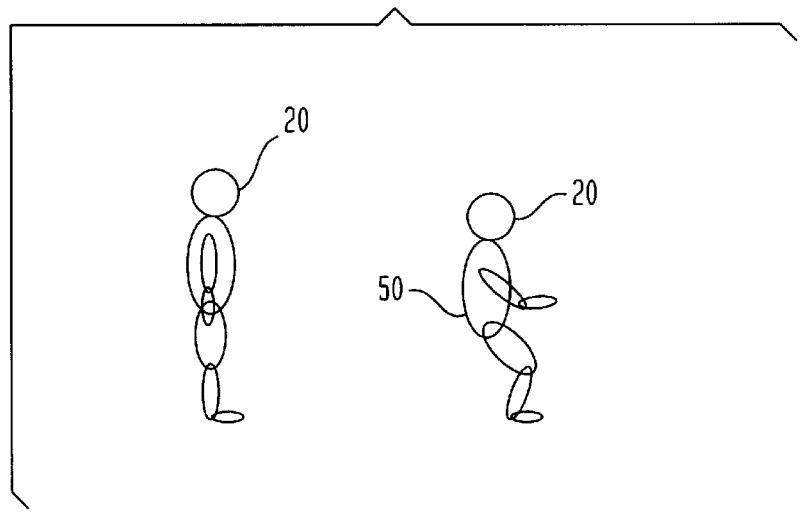
FIG. 5 is a schematic side view of the third exercise protocol (i.e., squatting), for use with the system of FIG. 1.

Referring to FIGS. 1, 5 and 8, in a third exercise protocol, the indicator 50 is attached to a belt which is positioned about the waist of the patient 20. Instructions are delivered from the computer processor 60 to the patient. The patient performs a squatting movement, starting from a straight position, bending down to a knees bent position and then standing straight again. This is performed without providing additional weighted resistance. Typically, the patient is not provided with handrails or other support devices but they can be provided, as the therapist deems appropriate.

As the patient lifts and lowers the platform or squats, the movement of the indicator is recorded, digitized, analyzed and put into a numerical patient data set. This patient data set is then compared to a second or base data set. In particular, the position of the indicator 50 (and thus the lifting platform 10 and the patient 20) is recorded over time. This information is digitized and analyzed to create a patient data set containing the velocity and acceleration of the indicator in the vertical direction during each portion of the repetition (i.e., either the upward motion and the downward motion from one end point to the other end point), the time period to complete each portion of each repetition, as well as any other parameters deemed relevant. Currently, it is preferred that the maximum velocity and the average velocity over a portion of the exercise (such as the portion of moving the lifting platform from ground to waist or from waist to ground one time), the time period for each portion of the exercise and the acceleration during the last ⅓ second of each portion of the exercise be calculated and put into a data set. Other parameters such as the time at which the peak velocity occurs during an exercise can also be calculated and included in the data set.

The patient data set for a given patient is compared with a standard or base data set. The standard data set is established by performing the same exercise protocols with a substantial number of known healthy people who are exerting a true effort. These healthy people also perform the exercise protocol with a faked effort. However, they were not provided with specific instructions regarding how to fake their effort. These healthy people are video taped and the movement of the indicator 50 is digitized and analyzed, as discussed above with regard to patients. Certain of the parameters calculated will be particularly consistent for the healthy people exerting a true effort, regardless of each person's particular strength or fitness level. Consequently, ranges can be developed for the parameters in which it is clear that a true effort is being given. Another range can be developed in which it is clear that a false or fake effort is being given. A certain other range (typically about 15% of those tested) can be developed in which it is unclear whether a true or false effort is being given. The parameters calculated for the patient during the exercise protocol are then compared to the parameters in the standard data set to determine in which range the patient falls. Thus, the comparison of the patient's parameters to the standard parameters provides the therapist with information concerning the effort of the patient as being true or faked. This "true" or "faked" nature of the patient's effort can also be termed "consistent" or "inconsistent", respectively.

As currently preferred, the standard data set is determined by sending a significant number (for example, 30 or more) of healthy people through the same exercise protocols as are to be performed by the test patients. The differences in the parameters for faked effort and true efforts are analyzed. It can be determined that a range of a given parameter (such as a mean velocity above a certain speed) is common to the vast majority of true efforts while another range of that same parameter (such as a mean velocity below a certain speed) is common to the vast majority of faked efforts. Between these two ranges, the parameters values do not provide a decisive result. As currently preferred, various parameters for each portion of the exercise protocol (i.e., the movement from one end point of the exercise motion to the other end point, such as the movement of the lifting platform from near ground level to waist level) are calculated. Knowing whether these efforts were true or faked, ranges for each parameter are developed based on the standard deviations from the means in which the efforts were true, in which they were faked and in which there were indeterminate. The degree of confidence is calculated for the parameter ranges by determining the P-values using paired T-tests, as one skilled in the art would appreciate. A discriminate analysis is also performed to ensure that the results did not occur by chance.

The parameters employed in the functional capacity assessment in accord with the instant invention all have a level of confidence above a selected value. Preferably, the selected parameters have ranges which indicate a level of confidence of 99.9% or better. The parameters having ranges which indicate a lower level of confidence are not currently used. As currently envisioned, the therapist does not have the ability to alter the parameter ranges. However, for certain clinical or experimental applications, it may be desirable to permit the therapist to alter the ranges and corresponding levels of confidence, as she sees fit. However, it is preferred that the computer processor 60 be provided with the ranges and then the computer display 63 or printer 64 merely display where in the ranges a particular patient's effort falls.

While the standard data set for use with the current invention has been developed using healthy people, this data set can also be developed using injured people as well. This data set can be composed of only injured people, only healthy people, or a combination of both. It may be desirable to develop standard data sets for specific groups of people, such as those with particular types of injuries, or for women and men separately, or for those with a particular occupation. This last example may be particularly useful when testing patients for a pre-employment screening.

In the current embodiment, the standard data sets have been developed for the floor-to-waist and the waist-to-overhead motions by testing 35 people over a series of repetitions adding three pounds to the container after each lift. A standard data set has similarly been developed for the squatting movement as well. The results of these tests are shown in FIGS. 6–8. The mean velocity, peak velocity, terminal acceleration (that is, the acceleration for the last ⅓rd of a second of a portion of the exercise protocol) and the time period for each portion of the exercise protocol is shown. The values for the different healthy test subjects are compared. Ranges are established for the true efforts and the faked efforts. The certainty or confidence level of those ranges can be calculated using traditional statistical techniques. While each standard parameter can be compared to the patient's parameters, it is preferred that the parameters having a high level of certainty only be compared. In this way, there is less likely to be an unclear determination.

Referring to FIG. 6, a typical chart is shown for the movement from the floor to waist, and back. During the first repetition (either in the ascending or descending portion), the peak velocity of the lifting platform is a good indicator of a true effort (also termed "consistent"). For example, when ascending (i.e., when lifting the platform from floor to waist), a peak velocity greater than 4.5 mm/frame corresponds to the healthy subjects, exerting a true effort. peak velocity less than 3.8 mm/frame corresponds to the health subjects, exerting a faked effort (also termed "inconsistent"). In between, the efforts are unclear (also termed "subconsistent"). Similarly, in the second and third repetitions, mean velocity and peak velocity have proven to be good measures of a true or faked effort. In the third repetition, the terminal acceleration has also proven to be a good measure of a true or faked effort. These parameters as calculated for the patient undergoing the same protocol can be compared to the chart to determine if the patient's effort is true or faked depending on the value of the patient's parameters.

FIG. 7 shows a similar chart for the floor to overhead movement. Again, as the patient goes through the exercise protocol, the parameters are calculated and compared to the standard data set, like that set forth in FIG. 7. This will indicate whether the patient is exerting a true or a faked effort.

FIG. 8 shows a similar chart for the squatting movement. As the patient goes through the squatting exercise protocol, the parameters are calculated and compared to the standard data set, like that set forth in FIG. 8. This will indicate whether the patient is exerting a true or a faked effort. It will be appreciated that the specific numerical ranges shown in the charts are exemplary. These values may change as more testing is done. Further, such charts can be developed for different exercises using different samples of people to develop the chart. While employing a chart is useful, it will be understood that the information of the standard data set can be arranged in other formats and still practice the invention. The charts need not be available to the therapist. Rather, the system can simply provide the therapist with the results of the comparison, such as how many of the parameters indicate that the patient is exerting a true effort and how many indicate that the patient is exerting a faked effort.

The functional capacity assessment system of the instant invention can also be employed to determine the maximal lifting ability of the patient. The various exercise protocols are performed for the floor to waist, waist to overhead and squatting exercises discussed above. The various parameters are calculated. The value of these parameters will change over the series of repetitions in a manner corresponding to the maximal lifting ability of the patient. For example, the mean velocity over a portion of the exercise protocol is likely to decrease over the series of repetitions. The rate of change of this mean velocity provides some indication of how much weight the patient could lift with a maximal effort. Consequently, the maximal effort which a patient can exert can be determined, in part, by comparing the parameters of the patient data set during consecutive repetitions. Additionally, the change in the parameters of the patient can be compared with those changes for healthy people of known maximal lifting ability in the standard or base data set. The change in performance of the patient can be compared to the change in performance of the standard data set. This difference can be used to determine the maximal lifting ability of the patient as compared to the maximal lifting ability of the healthy people in the standard data set.

In a similar manner, the parameters of the patient data set can be compared to the same parameters for subsequent repetitions by the same patient, or to the same parameters of the standard data set to determine the length of time during which the patient will be able to perform an exercise, that is, the patient's endurance.

The current system provides a more objective assessment technique than the current techniques employed by physical therapists. However, it will be appreciated that this new assessment technique can be used in conjunction with already accepted (albeit more subjective) techniques. For example, a weighted average can be developed based on this new technique as well as the more traditional techniques. The patient's performance in the first exercise protocol (lifting the weight from the floor to the waist and back again) has resulted in twelve measurements which indicate a real versus fake effort with adequate confidence (see FIG. 6). A patient is given one point for each effort which is determined to be real or consistent (i.e., falls within the pre-established numerical range for true efforts). Similarly, there are seven measures from the second protocol where the lifting platform is lifted from the waist to overhead and returned which provides a sufficient confidence level in the indication of consistency (see FIG. 7). Again, the patient is given one point for each parameter in which is determined to be in the consistent or real range (i.e., falls within the pre-established numerical range for true efforts). Similarly, the patient is given one true point for each parameter that falls within the range while performing squats (see FIG. 8). The points from these exercises are each multiplied by 2.5. This is combined with a measurement of grip consistency, as is well known in the art, multiplied by 11.5. The various observable non-organic signs are determined by the therapist to either be consistent or not consistent. If consistent, an additional 10 points is added to the total. Twenty-eight aspects of physical capacity are measured. The results which indicate a consistent or true effort are awarded 0.75 points and added to the total.

Employing this averaging technique, a patient who performs a perfectly consistent effort would total 100 points. A range has been established that a patient who receives 70 points is likely to be providing a consistent effort while a patient who receives less than 50 points is likely to be providing a fake or inconsistent effort. Of course, these ranges can be changed as experience dictates.

It will be appreciated that the therapist can employ the instant invention with other more traditional testing protocols. For example, a surface EMG can be used to determine the fatigue rate of a patient which in turn can indicate the patient's ability to perform various activities such as sitting, standing or typing over extended periods of time. The results of such testing can be incorporated into a report generated by the computer processor of the instant invention. Further, these results can be used by the therapist in reporting the nature and scope of the physical capacity of a given patient.

While this invention has been described with reference to specific embodiments disclosed herein, it is not confined to the details set forth and the patent is intended to include modifications and changes which may come within and extend from the following claims.

I claim:

1. A method of objectively testing the consistency of effort of a patient undergoing a functional capacity assessment by performing a selected exercise protocol over a range of motion and a limited resistance, the method comprising:

applying a selected number of indicators at selected points with respect to the patient;

directing the patient through the exercise protocol;

capturing the patient's movements on a video record;

digitizing the video record to obtain a digitized video record including the position of the indicators during the exercise protocol in at least a first direction;

tracking the motion of the indicators in the digitized video record in at least the first direction over time;

developing a patient data set including numerical performance parameters based, at least in part, on the position and the time of each indicator during the exercise protocol;

comparing the numerical performance parameters of the patient data set to at least a first range and a second range of a base data set, wherein the base data set comprises numerical ranges of performance parameters for subjects undergoing the exercise protocol, wherein the first range corresponds to the subjects exerting a true effort and wherein the second range corresponds to the subjects exerting a faked effort; and determining the consistency of effort of the patient based, at least in part, on the comparison of the patient data set with the base data set, wherein an effort is consistent if the numerical performance parameters of the patient data set fall within the first range and wherein an effort is inconsistent if the numerical performance parameters of the patient data set fall within the second range.

2. A method of objectively testing the functional capacity of a patient over a range of motion and a limited resistance, the method comprising:

applying a selected number of indicators at selected points with respect to the patient wherein at least one indicator is on a lifting platform;

directing the patient through a series of exercise movements which include lifting the lifting platform;

capturing the patient's movements on a video record;

digitizing the video record;

tracking the motion of the indicators in the digitized video record;

developing a patient data set including performance parameters based, at least in part, on the position and the time of each indicator during the movements;

comparing the patient data set to a base data set; and determining the functional capacity of the patient based, at least in part, on the comparison of the patient data set with the base data set.

3. The method of claim 2 wherein the base data set comprises performance parameters of healthy patients directed through the exercise movements.

4. The method of claim 3 wherein the functional capacity of the patient is the nature of the patient's effort as being true.

5. The method of claim 3 wherein the functional capacity of the patient is the nature of the patient's effort as being faked.

6. The method of claim 1 wherein the base data set comprises performance parameters calculated from the exercise movements performed by the patient directed through the exercise movements at a different time.

7. The method of claim 6 wherein the functional capacity of the patient is a measure of the maximal lifting ability of the patient.

8. The method of claim 1 wherein the functional capacity of the patient is a measure of the maximal lifting ability of the patient.

9. The method of claim 1 further comprising providing a selected resistance to the series of movements.

10. The method of claim 9 further comprising altering the resistance during the series of movements.

11. The method of claim 10 wherein the resistance is increased at a predetermined, controlled rate during the series of movements.

12. The method of claim 1 wherein developing the patient data set comprises calculating a first derivative with respect to time of the position of the indicators in at least the first direction.

13. The method of claim 12 further comprising determining an average first derivative over a portion of the series of the exercise movements, which average first derivative is a patient performance parameter that is compared to a base average first derivative in the first direction in the base data set.

14. The method of claim 12 further comprising determining a peak first derivative over a portion of the series of the exercise movements, which peak first derivative is a patient performance parameter that is compared to a base peak first derivative in the base data set.

15. The method of claim 1 wherein developing the data set comprises calculating a second derivative with respect to time of the position of the indicators in at least the first direction.

16. The method of claim 15 further comprising determining a terminal second derivative over a portion of the series of the exercise movements, which terminal second derivative is a patient performance parameter that is compared to a base terminal second derivative in the base data set.

17. The method of claim 1 wherein the indicator is attached to a box and the series of exercise movements comprise grasping a handle attached to the box, bending at the waist, moving the handle from near a ground level to a waist level, and returning the handle to near ground level.

18. The method of claim 1 wherein the indicator is attached to a box and the series of exercise movements comprise grasping a handle attached to the box, moving the handle from waist level to an overhead position, and returning the handle to waist level.

19. The method of claim 1 wherein the indicator is attached at the waist of the patient's body and wherein the exercise movements comprise starting at a standing position, squatting, and then standing again.

20. A method for assessing the functional capacity of a a patient by moving a lifting platform over a predetermined series of exercise movements, the method comprising:

moving by the patient of the lifting platform from a first level to a second level;

adding a selected resistance to the lifting platform;

moving by the patient of the lifting platform from the first level to the second level against the selected resistance;

recording the motion of the lifting platform during the moving by the patient on a motion record;

creating a patient data set including selected performance parameters corresponding, at least in part, to the position of the lifting platform over time during the moving by the patient;

comparing the data set with a standard data set;

determining the functional capacity of the patient based at least in part, on the comparison of the patient data set with the standard data set;

wherein the motion of the lifting platform is recorded as pictures by a video tape camera, the method further comprising digitizing the pictures into digitized information, and storing the digitized information in a computer memory;

wherein creating the patient data set includes determining the speed of the lifting platform in a vertical direction;

further comprising creating the standard data set including:

directing a limited group of people to exert a true effort;

lifting by the limited group of the lifting platform from the first level to the second level; and determining ranges of performance parameters indicative of a true effort to a selected level of statistical confidence;

wherein creating the standard data set further comprises:

directing a limited group of people to exert a false effort;

lifting by a limited group of the lifting platform from a first level to a second level; and determining ranges of performance parameters indicative of a false effort to a selected level of statistical confidence.

21. The method of claim 20 wherein comparing the patient data set with the standard data set includes comparing the performance parameters of the patient data set with the false effort range.

22. The method of claim 20 wherein determining the functional capacity of the patient includes determining whether the patient is exerting a true effort or a false effort based on whether the patient performance parameters fall within the true effort range or the false effort range.

23. A method of objectively testing the functional capacity of a patient over a range of motion and a limited resistance, the method comprising:

directing the patient through a series of exercise movements;

capturing the patient's movements on a video record;

digitizing the video record;

tracking the motion of a point with respect to the patient in the digitized video record;

developing a patient data set including performance parameters based, at least in part, on the position and the time of the point during the movements;

comparing the patient data set to a first base data set and a second base data set; and determining the functional capacity of the patient based, at least in part, on the comparison of the patient data set with the first base data set and the second base data set;

wherein the first base data set comprises performance parameters of healthy patients exerting a true effort directed through the exercise movements;

and wherein the second base data set comprises performance parameters of healthy patients exerting a faked effort directed through the exercise movements.

24. The apparatus of claim 23 wherein the functional capacity of the patient is the nature of the patient's effort as being true.

25. The apparatus of claim 23 wherein the functional capacity of the patient is the nature of the patient's effort as being faked.

* * * * *